(12) United States Patent
Bar Shalom (10) Patent No.: US 9,131,993 B2
(45) Date of Patent: Sep. 15, 2015

(54) DENTAL ABUTMENT WITH A FLAT CONNECTION

(75) Inventor: Eliezer Bar Shalom, Nir-Galim (IL)

(73) Assignee: A.B. Dental Devices Ltd., Nir Galim (IL)

( * ) Notice: Subject to any disclaimer, the term of this patent is extended or adjusted under 35 U.S.C. 154(b) by 908 days.

(21) Appl. No.: 12/867,169

(22) PCT Filed: Mar. 1, 2009

(86) PCT No.: PCT/IL2009/000229
§ 371 (c)(1),
(2), (4) Date: Aug. 11, 2010

(87) PCT Pub. No.: WO2009/107140
PCT Pub. Date: Sep. 3, 2009

(65) Prior Publication Data
US 2010/0311012 A1 Dec. 9, 2010

Related U.S. Application Data

(60) Provisional application No. 61/064,306, filed on Feb. 27, 2008.

(51) Int. Cl.
*A61C 8/00* (2006.01)

(52) U.S. Cl.
CPC ............. *A61C 8/005* (2013.01); *A61C 8/0069* (2013.01); *A61C 8/0075* (2013.01); *A61C 8/0054* (2013.01); *A61C 8/0068* (2013.01)

(58) Field of Classification Search
USPC .................................................. 433/172–176
See application file for complete search history.

(56) References Cited

U.S. PATENT DOCUMENTS 5,073,111 A 12/1991 Daftary
5,108,288 A * 4/1992 Perry ............................ 433/173

(Continued)

FOREIGN PATENT DOCUMENTS

DE 42 38 383 7/1994
DE 202006016557 4/2007

(Continued)

OTHER PUBLICATIONS

International Search report for PCT/IL2009/000229 dated Oct. 21, 2009.

(Continued)

*Primary Examiner* — Yogesh Patel
(74) *Attorney, Agent, or Firm* — Pearl Cohen Zedek Latzer Baratz LLP (57) ABSTRACT

A system, an abutment, a dental implant, kits and a method for implanting a prosthesis onto a jaw of a patient. The proximal end of the abutments is a flat connection of a predefined shape that is circularly symmetrical with a proximad decreasing radius. The prosthesis is attached to the distal ends of the abutments, and each abutment corresponds to a dental implant in the jaw. The dental implants are not all parallel to each other and may form any angle between them. The flat connection allows substantial tolerance in attaching the prosthesis to the dental implants. The predefined form may be a proximal disc connected to a distal truncated cone, wherein the proximal disc is congruent to the proximal face of the truncated cone. One system comprises abutments, dental implants, elastic supporting elements and extension elements.

8 Claims, 5 Drawing Sheets

(56) References Cited

U.S. PATENT DOCUMENTS

| | | | |
|---|---|---|---|
| 5,169,309 A | 12/1992 | Staubli et al. | |
| 5,427,906 A * | 6/1995 | Hansen | 433/173 |
| 5,439,380 A * | 8/1995 | Marlin | 433/172 |
| 5,527,182 A * | 6/1996 | Willoughby | 433/172 |
| 5,674,072 A | 10/1997 | Moser et al. | |
| 5,810,592 A * | 9/1998 | Daftary | 433/173 |
| 6,168,436 B1 * | 1/2001 | O'Brien | 433/173 |
| 6,827,575 B1 * | 12/2004 | Jorneus | 433/174 |
| 2001/0044095 A1 | 11/2001 | Rizzo | |
| 2005/0136378 A1 * | 6/2005 | Ennajimi et al. | 433/173 |
| 2005/0153261 A1 * | 7/2005 | Chang | 433/173 |
| 2006/0141418 A1 * | 6/2006 | Heo | 433/173 |
| 2007/0099153 A1 | 5/2007 | Fromovich | |
| 2007/0111162 A1 * | 5/2007 | Laux | 433/173 |
| 2009/0298013 A1 * | 12/2009 | Baruc | 433/174 |

FOREIGN PATENT DOCUMENTS

| | | |
|---|---|---|
| EP | 525296 A1 * | 2/1993 |
| FR | 2 863 478 | 6/2005 |
| WO | 01-97706 | 12/2001 |
| WO | 03/075783 | 9/2003 |

OTHER PUBLICATIONS

Written Opinion of the International Searching Authority for PCT/IL2009/000229 dated Oct. 21, 2009.

International Preliminary Report on Patentability (IPRP) for PCT/IL2009/000229 dated May 31, 2010.

Office Action of IL Application No. 207464 dated Dec. 29, 2013.

* cited by examiner

DENTAL ABUTMENT WITH A FLAT CONNECTION

CROSS REFERENCE TO RELATED APPLICATION

This US patent application claims priority to PCT patent application Ser. No. PCT/IL2009/000229 filed on Mar. 1, 2009, which is incorporated by reference herein.

BACKGROUND

1. Technical Field

The present invention relates to the field of medical appliances, and more particularly, the present invention relates to dental implants.

2. Discussion of Related Art

Dental prostheses are supported by abutments connected to them, which are attached to dental implants in the patient's jaw. The method of attaching the abutment to the implants limits the cases in which prostheses are applicable and the geometrical configuration of the dental implants.

Prior to setting forth the background of the related art, it may be helpful to set forth definitions of certain terms that will be used hereinafter.

The term "standard dental implant" as used herein in this application, is defined as any dental implant with an inner cavity such as internal hex, internal octagon or internal star.

BRIEF SUMMARY

Embodiments of the present invention provide a system for implanting a prosthesis onto a jaw of a patient comprising a plurality of abutments and a plurality of dental implants. Each abutment comprises a proximal end and a distal end, wherein the proximal end of at least one of the plurality of abutments is a flat connection of a predefined shape that is circularly symmetrical with a proximad decreasing radius. Each dental implant comprises a proximal end, a distal end and a length axis. The prosthesis is attached to the distal ends of the plurality of abutments, and each abutment corresponds to a dental implant in the jaw. The dental implants are not all parallel to each other, and the flat connection allows substantial tolerance in attaching the prosthesis to the dental implants.

Accordingly, according to an aspect of the present invention, there is provided a system, wherein the predefined shape comprises a proximal disc connected to a distal truncated cone, and wherein the proximal disc is congruent to the proximal face of the truncated cone.

Accordingly, according to another aspect of the present invention, there is provided a system, wherein the distal end of at least one of the plurality of dental implants has the form of a socket exhibiting a predefined socket shape fitting to receive the flat connection.

Accordingly, according to yet another aspect of the present invention, there is provided a system, wherein the prosthesis comprises at least one supporting element to which the distal ends of the plurality of abutments are attached. The supporting elements exhibit a predefined measure of flexibility arranged to allow elastically deforming the prosthesis to facilitate attaching the prosthesis to the jaw with the substantial tolerance. The predefined form of the flat connection is selected such as to enable connecting the proximal end of each of the plurality of abutments to the corresponding dental implant by utilizing the predefined measure of flexibility. In embodiments, the length axes of at least two of the plurality of dental implants form an angle greater than 20 degrees.

Embodiments of the present invention provide an abutment for supporting a prosthesis. One abutment comprises a proximal end and a distal end, wherein the proximal end is a flat connection of a predefined shape that is circularly symmetrical with a proximad decreasing radius.

Embodiments of the present invention provide a dental implant for receiving an abutment. One dental implant comprises a proximal end and a distal end, wherein the distal end is formed to a circularly symmetrical flat socket with a distad increasing inner radius and exhibits a predefined socket shape.

Embodiments of the present invention provide a kit for supporting a prosthesis comprising an abutment and a dental implant. One abutment comprises a proximal end and a distal end and exhibits a length axis, wherein the proximal end is a flat connection of a predefined shape that is circularly symmetrical with a proximad decreasing radius. One dental implant comprises a proximal end and a distal end and exhibits a length axis. The distal end of the abutment is arranged to be attached to the prosthesis. The flat connection is shaped such as to allow connecting the proximal end of the abutment to the distal end of the dental implant such that an angle is formed between the length axis of the abutment and the length axis of the dental implant. The flat connection is shaped such as to allow substantial tolerance in respect to the angle.

Accordingly, according to an aspect of the present invention, there is provided a kit, further comprising an extension element comprising a proximal end and a distal end. The proximal end of the extension element is arranged to be connected to the distal end of the dental implant and the distal end of the extension element is arranged to be connected to the proximal end of the abutment. The distal end of the extension element may have the form of a socket exhibiting a predefined socket shape fitting to receive the flat connection of the abutment.

Embodiments of the present invention provide a kit for implanting a prosthesis onto a plurality of dental implants comprising a distal end, a proximal end and a length axis, and implanted in a not fully parallel manner in a jaw of a patient. One kit comprises a plurality of abutments. At least one of the abutments comprises a proximal end and a distal end and exhibiting a length axis, wherein the proximal end is a flat connection of a predefined shape that is circularly symmetrical with a proximad decreasing radius. The prosthesis is attached to the distal ends of the plurality of abutments, and each abutment corresponds to one of the plurality of dental implants in the jaw. The plurality of dental implants are not all parallel to each other. The flat connection allows substantial tolerance in attaching the prosthesis to the plurality of dental implants.

Accordingly, according to an aspect of the present invention, there is provided a kit, further comprising at least one supporting element attachable to the prosthesis, to which the distal ends of the plurality of abutments are attached. The supporting element exhibits a predefined measure of flexibility arranged to allow elastically deforming the prosthesis to facilitate attaching the prosthesis to the jaw with the substantial tolerance. The predefined form of the flat connection is selected such as to enable connecting the proximal end of each of the plurality of abutments to the corresponding dental implant by utilizing the predefined measure of flexibility.

Embodiments of the present invention provide a method for implanting a prosthesis onto a jaw of a patient comprising: implanting a plurality of dental implants into the jaw, wherein the location and position of each dental implant are determined by considerations related to the bone structure of the jaw; connecting a plurality of abutments to the prosthesis, wherein the prosthesis is attached to the distal ends of the plurality of abutments, and each abutment corresponds to a dental implant in the jaw; and connecting the prosthesis to the jaw such that each abutment is attached to the corresponding dental implant. At least one of the plurality of abutments exhibits a proximal end that is flat connection of a predefined shape that is circularly symmetrical with a proximad decreasing radius. The flat connection allows substantial tolerance in the connecting the abutments to the dental implants. The substantial tolerance facilitates the connecting the prosthesis to the jaw.

Accordingly, according to an aspect of the present invention, there is provided a method, further comprising elastically deforming the prosthesis such as to utilize the substantial tolerance allowed by the flat connection to facilitate the connecting the prosthesis to the jaw.

Accordingly, according to another aspect of the present invention, there is provided a method, further comprising measuring the location of the dental implants in the jaw utilizing a plurality of transfer abutments; and planning the locations of the abutments on the prosthesis utilizing a plurality of implant analogs locate din relation to said measuring the location of the dental implants in the jaw utilizing the transfer abutments. Each transfer abutments comprises a proximal end and a distal end, and the proximal end of at least one of the plurality of transfer abutments is a flat connection of a predefined shape that is circularly symmetrical with a proximad decreasing radius.

Accordingly, according to yet another aspect of the present invention, there is provided a method, further comprising applying at least one extension element to facilitate the connecting the prosthesis to the jaw such that each abutment is attached to the corresponding dental implant, and wherein each extension element is arranged to connect one of the abutments to the corresponding dental implant and thereby enabling the connecting.

These, additional, and/or other aspects and/or advantages of the present invention are: set forth in the detailed description which follows; possibly inferable from the detailed description; and/or learnable by practice of the present invention.

BRIEF DESCRIPTION OF THE DRAWINGS

The present invention will be more readily understood from the detailed description of embodiments thereof made in conjunction with the accompanying drawings of which.

DETAILED DESCRIPTION

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

Figure 1:
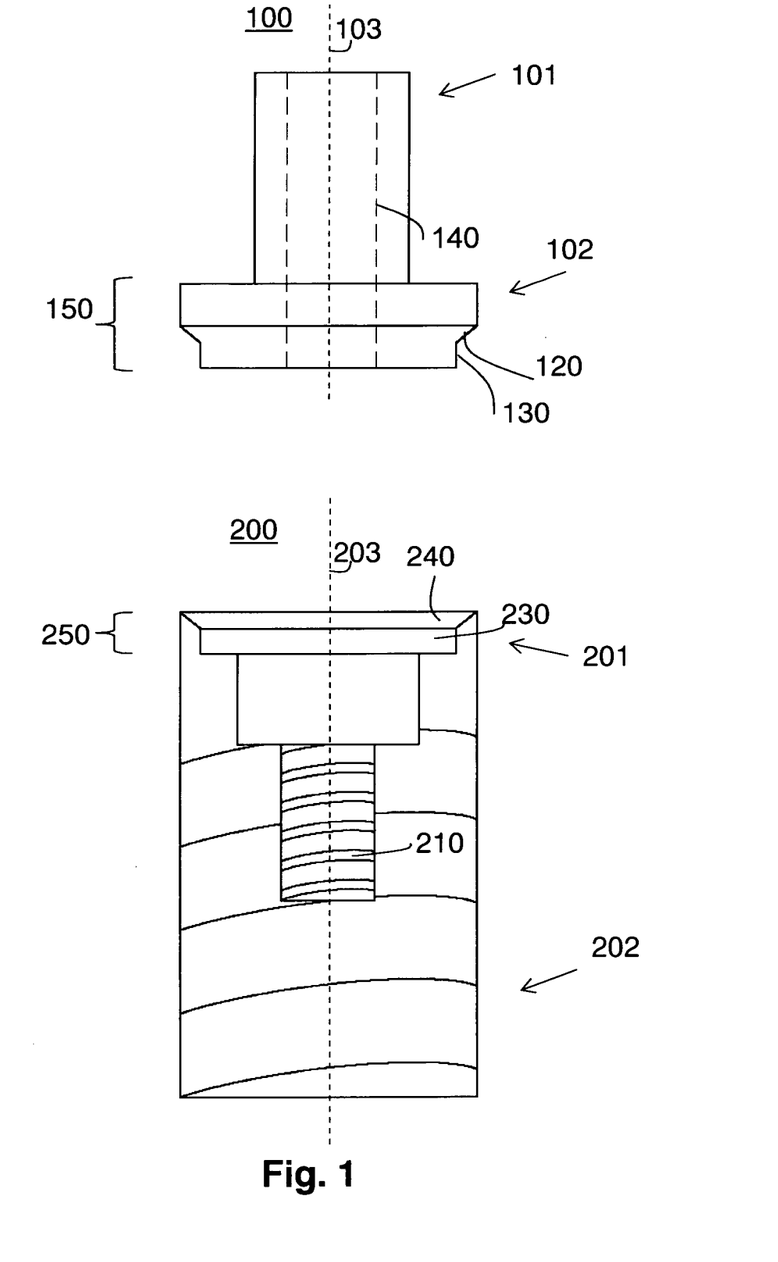
FIG. 1 is an illustration of a kit comprising an abutment for supporting a prosthesis and a dental implant for receiving abutment according to some embodiments of the invention.

FIG. 1 is an illustration of a kit comprising an abutment 100 for supporting a prosthesis 310 and a dental implant 200 for receiving abutment 100 according to some embodiments of the invention. Abutment 100 comprises a proximal end 102 and a distal end 101, as well as a length axis 103. Dental implant 200 comprises a proximal end 202 and a distal end 201, as well as a length axis 203. Dental implant 200 is implanted into the jaw. Abutment 100 is connected to dental implant 200 by a screw driven through a hole 140 having an internal screw thread and connected to a cavity 210 with an internal screw thread in dental implant 200. Proximal end 102 of abutment 100 is a circularly symmetrical flat connection 150 with a proximad decreasing radius. Distal end 201 of dental implant 200 has the form of a socket 250 fitting to receive flat connection 150.

According to some embodiments of the invention, flat connection 150 has the form of at least one truncated cone connected to at least one disc. Socket 250 may have a form fitting flat connection 150, wherein flat connection 150 has the form of at least one truncated cone connected to at least one disc.

According to some embodiments of the invention, flat connection 150 has the form of a proximal disc 130 connected to a distal truncated cone 120, wherein proximal disc 130 is congruent to the proximal face of truncated cone 120. The thickness of proximal disc 130 may be between 0.05 mm and 0.6 mm, between 0.1 mm and 0.3 mm, or approximately around 0.2 mm.

According to some embodiments of the invention, distal end 201 of dental implant 200 is formed to circularly symmetrical flat socket 250 with a distad increasing inner radius. According to some embodiments of the invention, socket 250 has a circularly symmetrical flat cavity comprising a disc shaped hollow 230 connected to a distal truncated cone 240, wherein disc shaped hollow 230 is congruent to the proximal face of truncated cone 240. The thickness of disc shaped hollow 230 may be between 0.05 mm and 0.6 mm, between 0.1 mm and 0.3 mm, or approximately around 0.2 mm.

According to some embodiments of the invention, the kit may be used to support the prosthesis either in combination with other dental implants and abutments or with other units of the kit. The kit may facilitate supporting the prosthesis at areas of the jaw which provide little or problematic support—such as large attachment angles and low bone support.

According to some embodiments of the invention, a further kit may comprise a plurality of abutments 100 for attaching a prosthesis onto a plurality of dental implants that are implanted in a not fully parallel manner in a jaw of a patient. This kit may be used to attach a prosthesis independently from implanting the dental implants. Proximal end 101 of at least one of the plurality of abutments 100 is a flat connection 150 of a predefined shape that is circularly symmetrical with a proximad decreasing radius. The prosthesis is attached to distal ends 102 of abutments 100, and each abutment 100 corresponds to a corresponding dental implant 200 in the jaw. Dental implants 200 must not be all parallel to each other, and any two may form angles up to 180 degrees between their length axes, and in particular larger angles than conventional maximal 10 to 20 degrees. Using flat connection 150 may allow implanting dental implants 200 in novel and more stable arrangements such as the "all on four" method comprising implanting dental implants 200 in crossing directions to avoid slipping of the prosthesis off dental implants 200 when these are implanted in a parallel manner. Flat connection 150 further allows substantial tolerance in attaching the prosthesis onto dental implants 200 due to the higher flexibility in placing them.

According to some embodiments of the invention, either kits may comprise one or more extension elements for facilitating the connection between abutments 100 and dental implants 200.

According to some embodiments of the invention, dental implant 200 may comprise a standard dental implant. Flat socket 250 may be shaped to fit the proximal end of a standard dental implant allowing some tolerance in respect to the exact fitting. The tolerance may allow an easier attachment of abutment 100 to a standard dental implant, either temporally or permanently.

Figure 2:
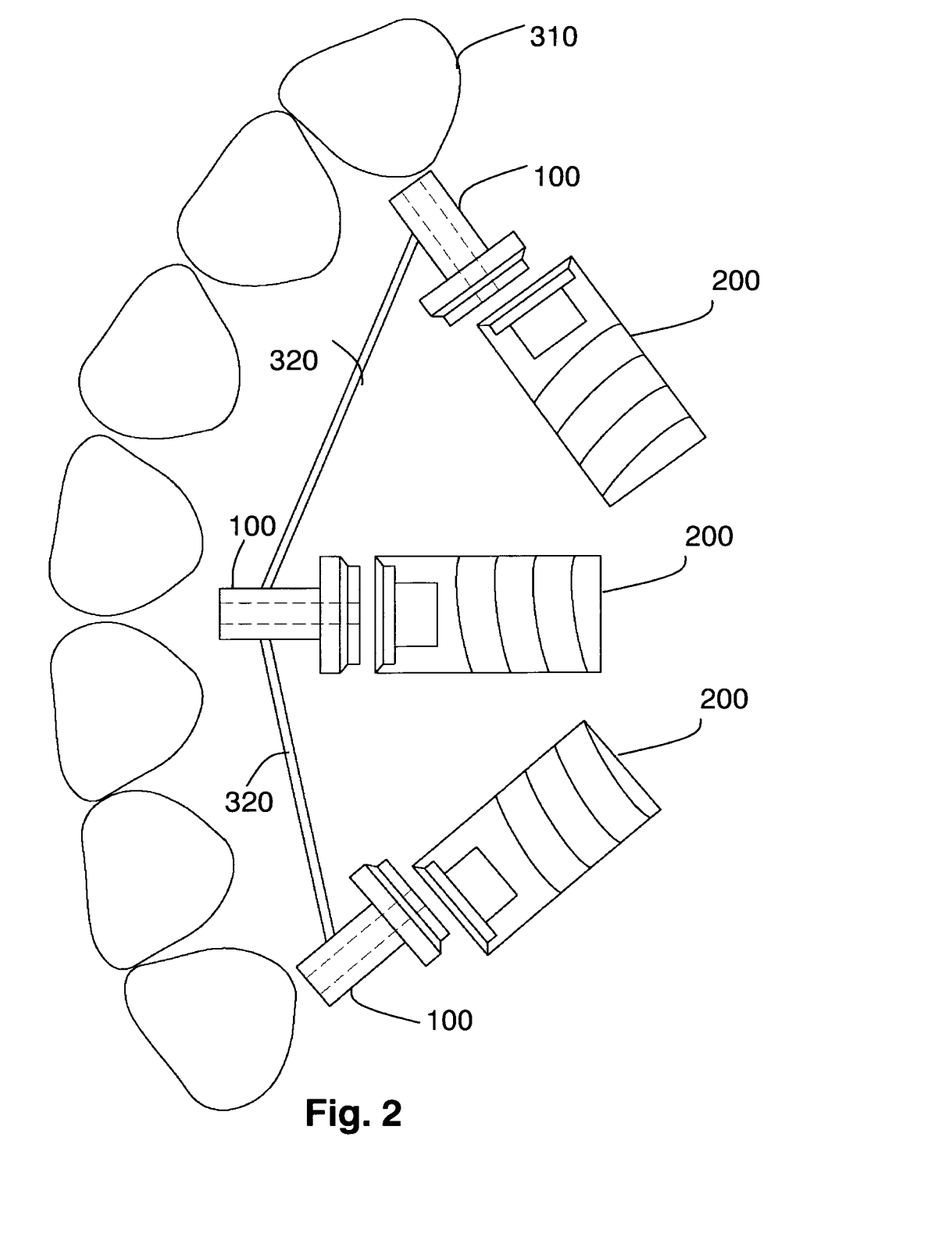
FIG. 2 is an illustration of a system for implanting a prosthesis onto a jaw of a patient according to some embodiments of the invention.

FIG. 2 is an illustration of a system for implanting a prosthesis 310 onto a jaw of a patient according to some embodiments of the invention. The system comprises a plurality of abutments 100 and a plurality of dental implants 200. Prosthesis 310 is attached to the distal ends of abutments 100, and each abutment 100 corresponds to a dental implant 200 in the jaw of the patient. The proximal ends of abutments 100 is a circularly symmetrical flat connection 150 with a proximad decreasing radius, and the distal end of dental implants 200 has the form of a socket 250 fitting to receive flat connection 150. Dental implants 200 at the top and at the bottom of FIG. 2 are slightly moved from their corresponding abutments 100 to illustrate that although the movement of abutments 100 with prosthesis 310 is rigid, due to flat connection 150 abutments 100 fit their corresponding dental implants 200.

According to some embodiments of the invention, prosthesis 310 comprises supporting elements 320 to which the distal ends of abutments 100 are attached. Supporting elements 320 may exhibit a predefined measure of flexibility arranged to allow elastically deforming prosthesis 310 to facilitate attaching it to the jaw with substantial tolerance. The predefined form of flat connection 150 is selected such as to enable connecting the proximal end of each of abutments 100 to the corresponding dental implant 200 by utilizing the predefined measure of flexibility. The flatness of flat connection 150 allows some tolerance to the exact positions of abutments 100 and together with the flexibility of supporting elements 320 facilitates an easier placement of abutments 100 and of prosthesis 310 as a whole—due to the fact that flat connection 150 is easier to attach to dental implant 200 than a standard deep connection requiring a closer fit.

According to some embodiments of the invention, some of dental implants 200 may be standard dental implants. Abutments 100 with flat connection 150 may be attached to these implants imperfectly, yet sufficiently to facilitate attaching prosthesis 310—either as a temporal or as a permanent prosthesis. Using standard dental implants with abutments 100 with flat connections 150 may allow improving prosthesis 310 attachment using existing dental implants and may raise the availability and applicability of the system.

According to some embodiments of the invention, flat connection 150 may be shaped such as to allow connecting the proximal ends of abutments 100 to the distal ends of dental implants 200, such that angles are formed between the length axes. Flat connections 150 may be shaped such as to allow substantial tolerance in respect to these angles thus supporting prosthesis 310 in cases in which standard abutments fail to provide support due to the required depth of fitting the standard abutment to the standard dental implant and the resulting exact attachment required.

According to some embodiments of the invention, the system and kits may further comprise transfer abutments and implant analogs for measuring and planning the implantation and attachment of the prosthesis. Transfer abutments may comprise a proximal flat connection, which is of a circularly symmetrical predefined shape with a proximad decreasing radius. The flat connection may facilitate an easier measurement of the locations of dental implants 200.

According to some embodiments of the invention, the system and kits may further comprise extension elements applied to facilitate connecting prosthesis 310 to the jaw such that each abutment 100 is attached to the corresponding dental implant 200. The extension elements are each arranged to connect one of abutments 100 to the corresponding dental implant 200. The proximal end of each extension element is arranged to be connected to the distal end of the corresponding dental implant 200 and the distal end of each extension element is arranged to be connected to the proximal end of the corresponding abutment 100. The extension may have distal sockets arranged to receive flat connection 150 of abutment 100.

Figure 3:
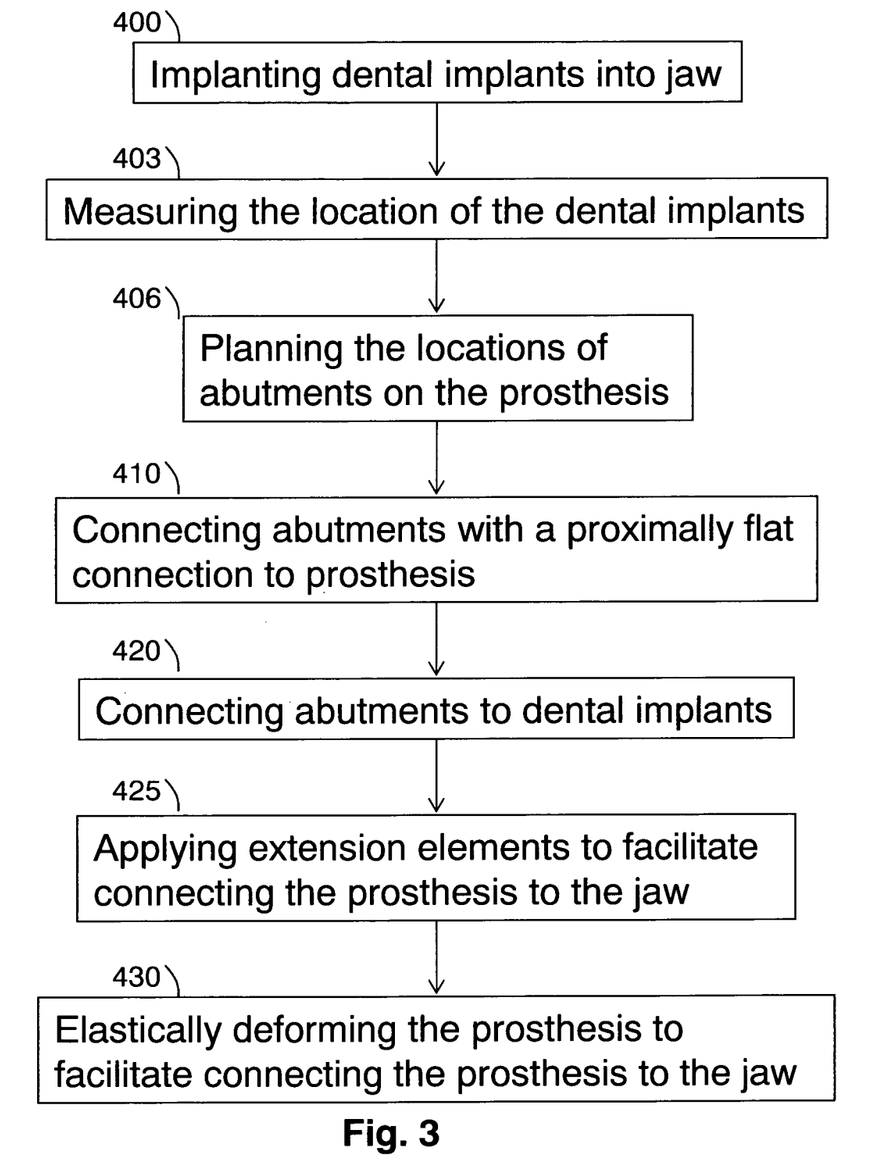
FIG. 3 is a high level schematic block diagram illustrating a method for implanting prosthesis onto a jaw of a patient according to some embodiments of the invention.

FIG. 3 is a high level schematic flowchart illustrating a method for implanting prosthesis 310 onto a jaw of a patient according to some embodiments of the invention. The method comprises the following steps: implanting a plurality of dental implants 200 into the jaw (step 400), wherein the location and position of each dental implant 200 are determined by considerations related to the bone structure of the jaw; connecting a plurality of abutments 100 with a proximally flat connection 150 (step 410) to prosthesis 310, wherein prosthesis 310 is attached to the distal ends of abutments 100, and each abutment 100 corresponds to a dental implant 200 in the jaw; and connecting prosthesis 310 in such a way, that each abutment 100 is attached to the corresponding dental implant 200 (step 420), wherein in case some abutments 100 do not fit their corresponding dental implants 200—the prosthesis 310 is elastically deformed to gain a fit (step 430, utilizing the substantial tolerance allowed by the flat). Flat connection 150 allows substantial tolerance in connecting abutments 100 to dental implants 200 (step 410). This tolerance is due to flat connection 150 at the proximal ends of abutments 100 in respect to a much deeper connection needed in regular abutments, that fit into hexagonal inner cavity 220 fully.

According to some embodiments of the invention, the proximal end of at least some of the abutments may comprise a circularly symmetrical flat connection with a proximad decreasing radius that exhibits a predefined shape. The flat connection may be shaped to allow substantial tolerance in connecting the abutments to the dental implants (step 420) that facilitates connecting (step 420).

According to some embodiments of the invention, implanting the dental implants into the jaw (step 400) may be carried out in various techniques, dental implants must not necessarily be all parallel to each other, and any two may form angles up to 180 degrees between their length axes. In particular implantation (step 400) may be carried out at larger angles than conventional maximal 10 to 20 degrees. Using flat connection while connecting the abutments to the dental implants (step 420) may allow implanting dental implants (step 400) in novel and more stable arrangements such as the "all on four" method comprising implanting dental implants (step 400) in crossing directions to avoid slipping of the prosthesis off the dental implants when these are implanted in a parallel manner. In general, a non parallel implantation (step 400) may enable an optimal use of hard bone structures in the jaw.

According to some embodiments of the invention, the method may further comprise elastically deforming the prosthesis (step 430) such as to utilize the substantial tolerance allowed by the flat connection to facilitate connecting the prosthesis to the jaw (step 420). This application utilizes the substantial tolerance allowed by the flat connection in attaching the prosthesis onto the dental implants (step 420) due to the higher flexibility in placing them (step 400).

According to some embodiments of the invention, the method may further comprise: measuring the location of the dental implants in the jaw utilizing transfer abutments (step 403); and planning the locations of the abutments on the prosthesis utilizing a plurality of implant analogs (step 406) located in relation to the measured location of the dental implants (step 403). Each transfer abutment comprises a proximal end and a distal end, and at least one of the transfer abutments comprises a flat connection at its proximal end, which is of a circularly symmetrical predefined shape with a proximad decreasing radius.

According to some embodiments of the invention, the method may further comprise applying extension elements (step 425) to facilitate connecting the prosthesis to the jaw such that each abutment is attached to the corresponding dental implant (step 420). The extension elements are each arranged to connect one of the abutments to the corresponding dental implant and thereby enabling their connecting.

The method may be used to attach a temporal prosthesis or to support attaching a prosthesis in cases of problematic bone support to the prosthesis, either due to reduced bone strength or due to problematic attachment angles and directions.

Figure 4:
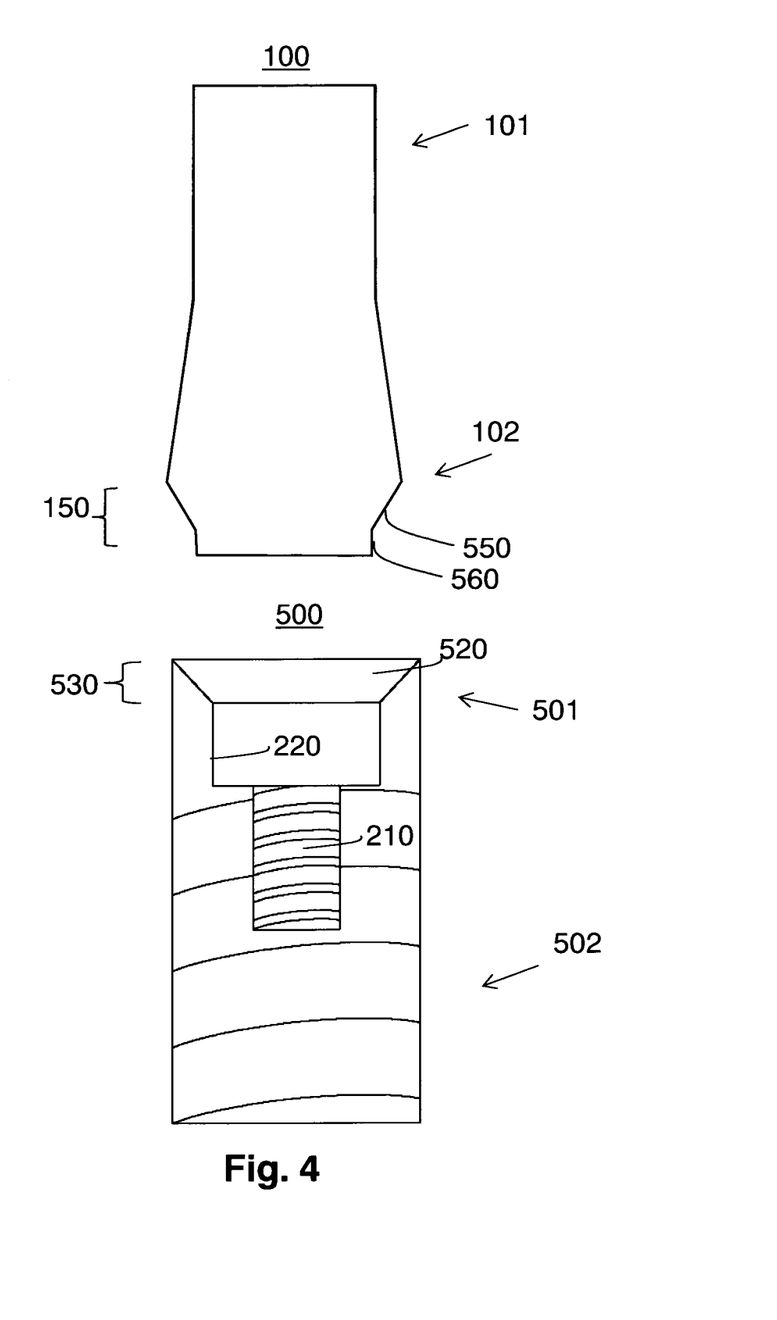
FIG. 4 is an illustration of an abutment for supporting prosthesis and a standard dental implant for receiving abutment according to some embodiments of the invention.

FIG. 4 is an illustration of an abutment 100 for supporting prosthesis 310 and a standard dental implant 500 for receiving abutment 100 according to some embodiments of the invention. Abutment 100 comprises a proximal end 102 and a distal end 101, as well as a length axis. Standard dental implant 500 comprises a proximal end 502 and a distal end 501, as well as a length axis. Standard dental implant 500 is connected to the jaw by a screw driven through a hexagonal inner cavity 220. The distal end of standard dental implant 500 comprises a cavity 520 formed as a truncated cone with a distad increasing radius. Proximal end 102 of abutment 100 is a circularly symmetrical flat connection 150 with a proximad decreasing radius. The proximal part of abutment 100 is a flat connection fitting to standard dental implant 500 and to the socket 530 at the distal end of abutment 500.

According to some embodiments of the invention, flat connection 150 has the form of a truncated cone 550 with a proximad decreasing radius. Hat connection 150 may be made to fit into the socket cone of a standard dental implant 500.

According to some embodiments of the invention, flat connection 150 has the form of a proximal disc 560 connected to a distal truncated cone 550. Truncated cone 550 has a proximad decreasing radius and a height equal or smaller than the distal cone of standard dental implant 500, and the face of disc 560 is inscribed within the hexagonal inner cavity 220 of standard dental implant 500 (e.g. in the case of the standard narrow implant of 3.75 mm diameter, the diameter of disc 560 may be 2.5 mm).

Figure 5:
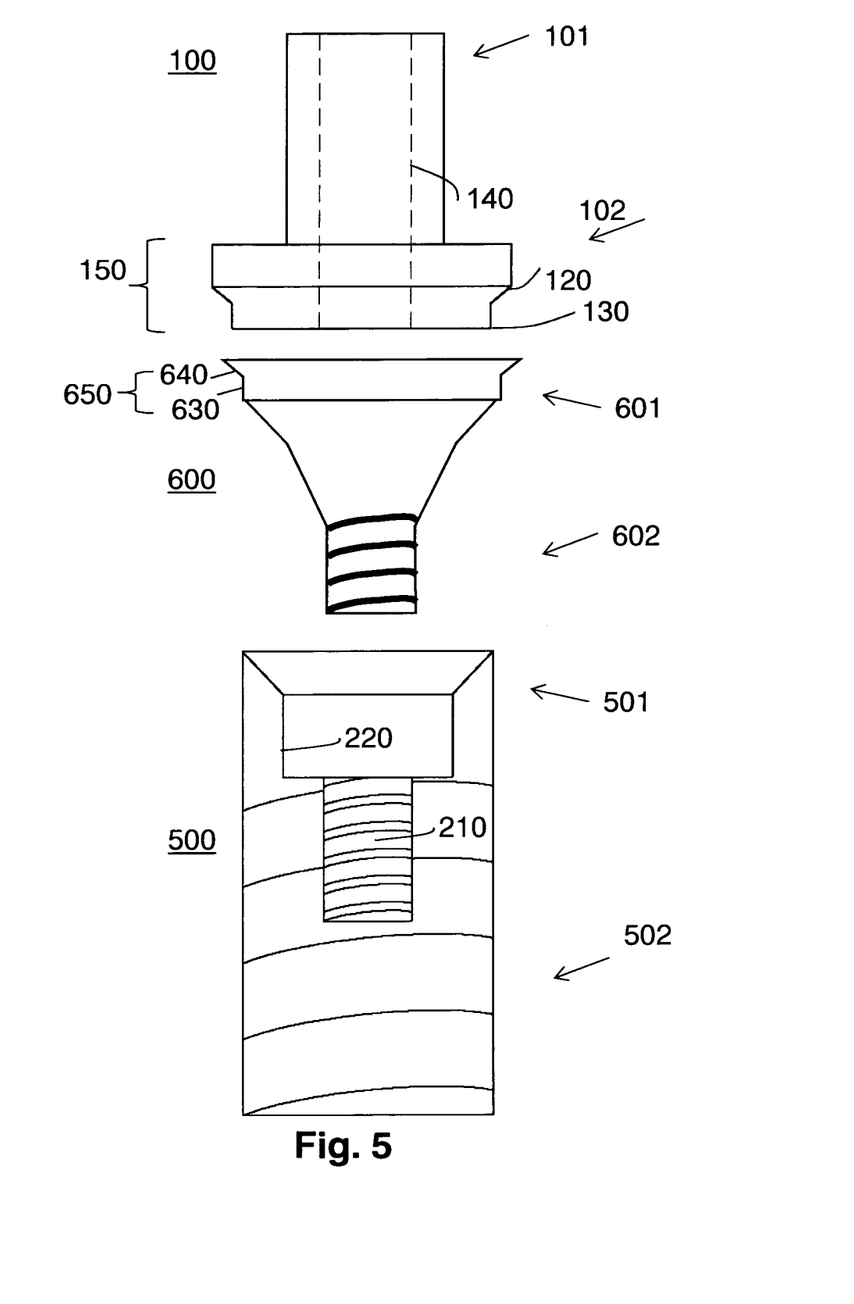
FIG. 5 is an illustration of an extension element for facilitating the connection between abutments and dental implants, according to some embodiments of the invention

FIG. 5 is an illustration of an extension element 600 for facilitating the connection between abutments 100 and dental implants 200, according to some embodiments of the invention. One or more extension elements 600 may be added to any of the kits or to the system to allow more flexibility in placing abutments 100 onto dental implants 200. Extension element 600 may comprise a proximal end 602 comprising a screw thread configured to be received by the internal screw thread in cavity 210 of dental implant 200 and a distal end 601 comprising a socket 650 to receive abutments 100.

According to some embodiments of the invention, proximal end 602 of each extension element 600 is arranged to be connected to distal end 501 of the corresponding dental implant 200 and distal end 601 of each extension element 600 is arranged to be connected to proximal end 102 of the one of abutments 100.

According to some embodiments of the invention, distal end 601 of extension element 600 may be formed to a circularly symmetrical flat socket 650 with a distad increasing inner radius. According to some embodiments of the invention, socket 650 has a circularly symmetrical flat cavity comprising a disc shaped hollow 630 connected to a distal truncated cone 640, wherein disc shaped hollow 630 is congruent to the proximal face of truncated cone 640. The thickness of disc shaped hollow 630 may be between 0.05 mm and 0.6 mm, between 0.1 mm and 0.3 mm, or approximately around 0.2 mm. socket 650 may have a predefined socket form select to receive and fit flat connection 150.

According to some embodiments of the invention, the kits may further comprise supporting elements 320 to which the distal ends of abutments 100 are attached. Supporting elements 320 may exhibit a predefined measure of flexibility arranged to allow elastically deforming prosthesis 310 to facilitate attaching it to the jaw with substantial tolerance. The predefined form of flat connection 150 is selected such as to enable connecting the proximal end of each of abutments 100 to the corresponding dental implant 200 by utilizing the predefined measure of flexibility. The flatness of flat connection 150 allows some tolerance to the exact positions of abutments 100 and together with the flexibility of supporting elements 320 facilitates an easier placement of abutments 100 and of prosthesis 310 as a whole—due to the fact that flat connection 150 is easier to attach to dental implant 200 than a standard deep connection requiring a closer fit.

In the above description, an embodiment is an example or implementation of the inventions. The various appearances of "one embodiment," "an embodiment" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions.

It is to be understood that the phraseology and terminology employed herein is not to be construed as limiting and are for descriptive purpose only.

The principles and uses of the teachings of the present invention may be better understood with reference to the accompanying description, figures and examples.

It is to be understood that the details set forth herein do not construe a limitation to an application of the invention.

Furthermore, it is to be understood that the invention can be carried out or practiced in various ways and that the invention can be implemented in embodiments other than the ones outlined in the description above.

It is to be understood that the terms "including", "comprising", "consisting" and grammatical variants thereof do not preclude the addition of one or more components, features, steps, or integers or groups thereof and that the terms are to be construed as specifying components, features, steps or integers.

If the specification or claims refer to "an additional" element, that does not preclude there being more than one of the additional element.

It is to be understood that where the claims or specification refer to "a" or "an" element, such reference is not be construed that there is only one of that element.

It is to be understood that where the specification states that a component, feature, structure, or characteristic "may", "might", "can" or "could" be included, that particular component, feature, structure, or characteristic is not required to be included.

Where applicable, although state diagrams, flow diagrams or both may be used to describe embodiments, the invention is not limited to those diagrams or to the corresponding descriptions. For example, flow need not move through each illustrated box or state, or in exactly the same order as illustrated and described.

Methods of the present invention may be implemented by performing or completing manually, automatically, or a combination thereof, selected steps or tasks.

The term "method" may refer to manners, means, techniques and procedures for accomplishing a given task including, but not limited to, those manners, means, techniques and procedures either known to, or readily developed from known manners, means, techniques and procedures by practitioners of the art to which the invention belongs.

The descriptions, examples, methods and materials presented in the claims and the specification are not to be construed as limiting but rather as illustrative only.

Meanings of technical and scientific terms used herein are to be commonly understood as by one of ordinary skill in the art to which the invention belongs, unless otherwise defined.

The present invention may be implemented in the testing or practice with methods and materials equivalent or similar to those described herein.

Any publications, including patents, patent applications and articles, referenced or mentioned in this specification are herein incorporated in their entirety into the specification, to the same extent as if each individual publication was specifically and individually indicated to be incorporated herein. In addition, citation or identification of any reference in the description of some embodiments of the invention shall not be construed as an admission that such reference is available as prior art to the present invention.

While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

What is claimed is:

1. A kit comprising:
    a first dental implant, the first dental implant having a length axis and a distal end comprising a socket and is fittable with a standard abutment that requires exact and full fitting with said socket; and
    a dental abutment comprising:
        a proximal end comprising a flat connection connectable to the first dental implant, wherein the flat connection has a circular symmetry, has a proximad decreasing radius and a specified thickness;
        an inner cavity arranged to allow an additional connection of the abutment to the first implant by a fastener; and
        a distal end connectable to a prosthesis,
    wherein the specified thickness is substantially smaller than said socket's depth of the first dental implant, such that upon connection of the dental abutment to the first implant less than a half of a volume of the socket is filled, the partial filling allowing flexibility in placing the dental abutment, and
    wherein the first dental implant is arranged to receive the dental abutment in said socket's volume that is less than a half filled upon connection of the dental abutment to the first implant, the partial filling allowing flexibility in placing the dental abutment, and
    wherein the flat connection allows tolerance in respect to angles formed between the length axes of the first dental implant and a second dental implant, and is arranged to enhance connectability of the dental abutment to the first dental implant in dental situations that limit a maneuverability of the dental abutment into the first dental implant, and to allow connecting the abutment to the first implant when a direct approach is not available by enabling use of a wide range of approach angles.

2. The kit of claim 1, wherein the flat connection is shaped as a truncated cone and the dental implant is a standard hex implant.

3. The kit of claim 1, wherein the flat connection is shaped as a disc proximally attached to a truncated cone, and wherein a distal end of the socket is shaped to receive the flat connection.

4. The kit of claim 1, wherein the flat connection is shaped as a truncated cone, and wherein a distal end of the socket is shaped to receive a flat connection shaped as a disc proximally attached to the truncated cone, thereby leaving a circular space between the socket and the flat connection.

5. The kit of claim 1, further comprising an extension element connectable to the dental abutment and to the dental implant, the extension element comprising at least one of: a proximal flat connection connectable to the dental implant, wherein the flat connection of the extension element has a circular symmetry, has a proximad decreasing radius and a specified thickness; and a distal socket arranged to receive the flat connection of the dental abutment.

6. A system comprising:
    at least one kit comprising a corresponding at least one dental abutment and at least a first dental implant, the first dental implant having a length axis and a distal end comprising a socket and is fittable with a standard abutment that requires exact and full fitting with said socket, wherein:
    the dental abutment comprises:
        a proximal end comprising a flat connection connectable to the first dental implant, wherein the flat connection has a circular symmetry, has a proximad decreasing radius and a specified thickness;
        an inner cavity arranged to allow an additional connection of the abutment to the first implant by a fastener; and
        a distal end connectable to a prosthesis,
    wherein the specified thickness is substantially smaller than said socket's depth of the first dental implant, such that upon connection of the dental abutment to the first implant less than a half of a volume of the socket is filled, the partial filling allowing flexibility in placing the dental abutment, and the first dental implant has a socket volume that is less than a half filled upon connection of the dental abutment to the first implant, the partial filling allowing flexibility in placing the dental abutment, a second dental implant having a length axis and a distal end comprising a socket and is fittable with a standard abutment that requires exact and full fitting with said socket;

wherein the flat connection allows tolerance in respect to angles formed between the length axes of the first and second dental implants, and is arranged to enhance connectability of the dental abutment to the first dental implant in dental situations that limit a maneuverability of the dental abutment into the first dental implant, and to allow connecting the abutment to the first implant when a direct approach is not available by enabling use of a wide range of approach angles; and a prosthesis connectable to the at least one dental abutment of the at least one kit and to a standard abutment fittable with a standard dental implant according to a dental planning, wherein the at least first and second dental implants are not parallel in the dental planning, wherein the at least one kit is usable to allow connecting the proximal end of the dental abutment of the kit to the distal end of the first dental implant, such that angles are formed between the length axes of the dental implants, and to allow tolerance in respect to these angles in cases in which standard abutments fail to provide support due to the required depth of fitting a standard abutment to a standard dental implant and the resulting exact attachment required.

7. The system of claim 6, wherein the prosthesis comprises at least one supporting element to which the distal ends of the abutments are attached, wherein the at least one supporting element exhibits a predefined measure of flexibility arranged to allow elastically deforming the prosthesis to facilitate attaching the prosthesis to the jaw, and wherein the flat connection is selected such as to enable connecting the proximal end of the at least one dental abutment having the flat connection to the dental implant by utilizing the predefined measure of flexibility.

8. The system of claim 6, wherein the at least one dental abutment forms an angle greater than 20 degrees to at least one of the standard abutments according to the dental planning.

* * * * *